United States Patent [19]
Hotier et al.

[11] Patent Number: 5,401,476
[45] Date of Patent: Mar. 28, 1995

[54] APPARATUS FOR THE SEPARATION OF P-XYLENE IN C₈ AROMATIC HYDROCARBONS WITH A SIMULATED MOVING BED ADSORPTION AND A CRYSTALLISATION

[75] Inventors: Gerard Hotier, Rueil Malmaison; Claude Roux Guerraz; Than Nguyen Thanh, both of Paris, all of France

[73] Assignee: Institut Francais du Petrole, Rueil Malmaison, France

[21] Appl. No.: 141,750

[22] Filed: Oct. 27, 1993

Related U.S. Application Data

[62] Division of Ser. No. 941,296, Sep. 4, 1992, Pat. No. 5,284,992.

[30] Foreign Application Priority Data

Sep. 5, 1991 [FR] France ................. 91 11004
Jul. 6, 1992 [FR] France ................. 92 08497
Jul. 6, 1992 [FR] France ................. 92 08498

[51] Int. Cl.⁶ .............................................. B01J 8/02
[52] U.S. Cl. .................................. 422/222; 422/256; 422/261; 422/281
[58] Field of Search ............... 422/216, 255, 256, 261, 422/281, 211, 222, 245; 585/805, 814, 825, 828, 831

[56] References Cited

U.S. PATENT DOCUMENTS

| | | | |
|---|---|---|---|
| 3,813,452 | 5/1974 | Bieser | 260/674 SA |
| 3,948,758 | 4/1976 | Bonacci et al. | 208/92 |
| 3,959,978 | 6/1976 | Lindley et al. | 62/58 |
| 4,118,429 | 10/1978 | Fritsch et al. | 260/674 SA |
| 4,402,832 | 9/1983 | Gerhold | 210/659 |
| 4,498,991 | 2/1985 | Oroskar | 210/659 |

FOREIGN PATENT DOCUMENTS

| | | |
|---|---|---|
| 0003622 | 8/1979 | European Pat. Off. |
| 2436076 | 2/1975 | Germany |
| 55-139327 | 10/1980 | Japan |
| 1420796 | 1/1976 | United Kingdom |

*Primary Examiner*—Amalia L. Santiago
*Attorney, Agent, or Firm*—Millen, White, Zelano & Branigan

[57] ABSTRACT

To continuously produce and separate high purity p-xylene from a C₈ aromatic hydrocarbon charge, successive use is made in combination of (1) a stage of separating low-purity p-xylene (75 to 98%) by simulated moving bed adsorption chromatography, with a ratio of the solvent to charge flow rates of 1.2 to 2.5; (2) a stage of purifying and washing the low-purity p-xylene by re-crystallization (−25 to +10° C.); (3) a stage of catalytic isomerization of the charge which has been p-xylene-depleted by the separating stage (1); and recovering an isomerate which is then recycled to the charge. The solvent for desorption in stage (1) and washing in stage (2) is advantageously toluene.

6 Claims, 1 Drawing Sheet

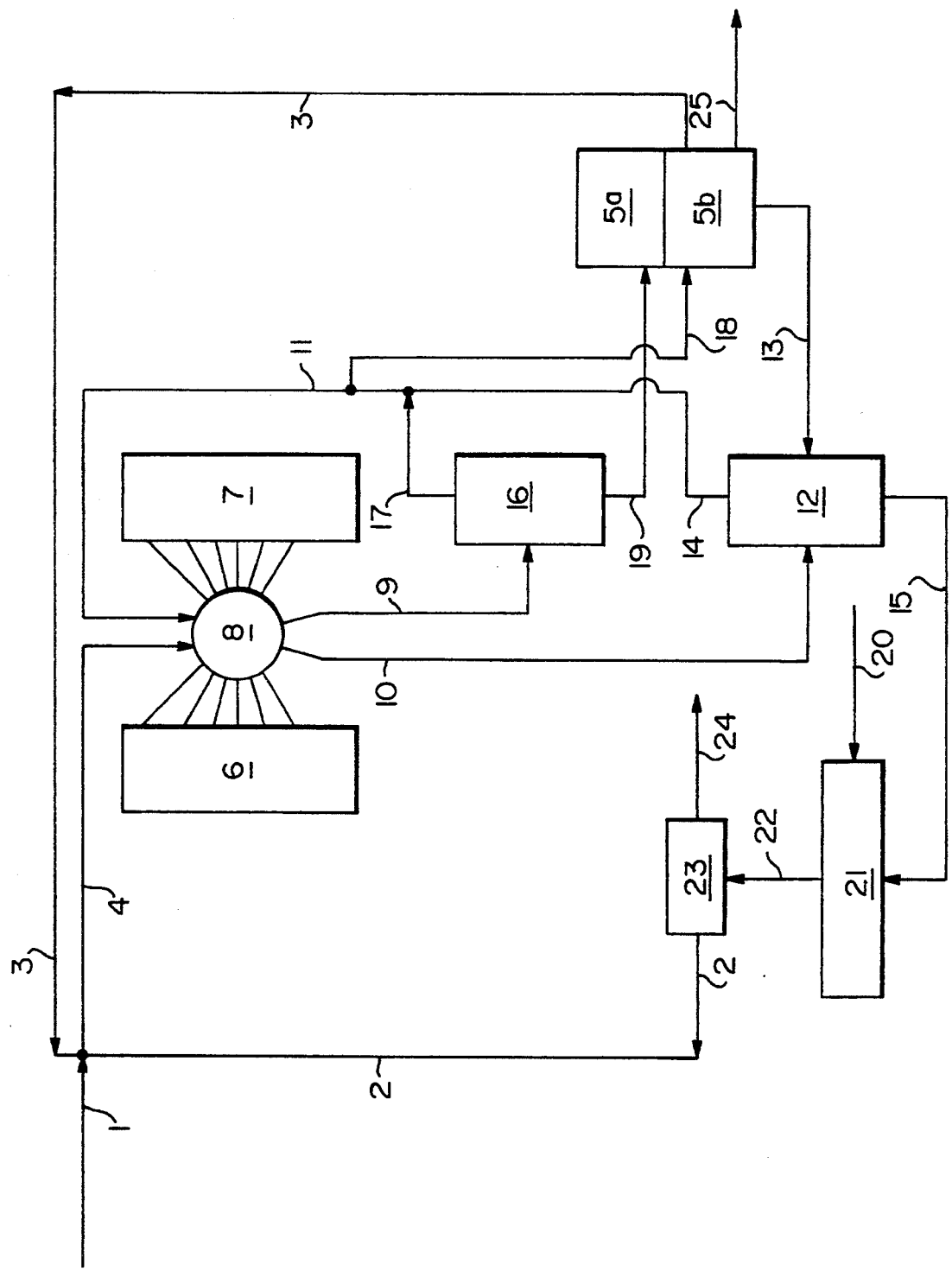

APPARATUS FOR THE SEPARATION OF P-XYLENE IN C<sub>8</sub> AROMATIC HYDROCARBONS WITH A SIMULATED MOVING BED ADSORPTION AND A CRYSTALLISATION This application is a divisional of application Ser. No. 07/941,296, filed Sep. 4, 1992, now U.S. Pat. No. 5,284,992.

BACKGROUND OF THE INVENTION

The present invention relates to an improved process and apparatus for the separation of $C_8$ aromatic hydrocarbons of p-xylene and at least one o-xylene, m-xylene, and ethyl benzene, to obtain synthesis-grade p-xylene, useful for producing terephthalic acid for example.

A known p-xylene separation method consists of carrying out a fractional crystallization. Among the presently used processes are those of Chevron, Krupp, Amoco, Mazuren and Arco (U.S. Pat. Nos. 3,177,255 and 3,467,724).

The Amoco and Arco processes use the following procedure. The charge containing at least 20% p-xylene is cooled from $-50°$ to $-70°$ C., which brings about crystallization. Part of the crystal cake, whose overall p-xylene content is 85 to 90% is separated by filtration, said cake being saturated with liquid and the mother liquor still containing 7 to 8% p-xylene. The crystal cake is remelted and cooled to $-10°$ C., which brings about recrystallization. After filtration, a new wet cake is obtained, together with a second mother liquor containing approximately 25 to 40% p-xylene. The cake is washed with toluene, which makes it possible to obtain a final purity of at least 99.5% after eliminating the toluene by distillation. The method liquors can undergo an isomerization treatment, or can be recycled with the charge in the second.

The other method for the separation of $C_8$ aromatic hydrocarbons and more particularly p-xylene from the xylene isomers and ethyl benzene is a so-called simulated countercurrent liquid chromatography method (U.S. Pat. No. 2,985,589), which uses the property of certain adsorbents and in particular zeolites to selectively adsorb p-xylene. The Parex and Aromax processes use this method. Reference can also be made to the simulated cocurrent liquid chromatography method described in U.S. Pat. No. 4,402,832.

The method of separating p-xylene by crystallization suffers from the major disadvantage that the maximum recovery level per pass is limited to approximately 60% as a result of the existence of eutectics between the p-xylene and the other $C_8$ aromatic hydrocarbons and it is consequently necessary to have a significant isomerization loop. Moreover, the cooling to $-65°$ C. leads to considerable energy costs.

Continuous liquid chromatography methods (e.g. simulated counter-current) have the following characteristics. If it is wished to simultaneously obtain a high purity of the p-xylene (approximately 99.5%) and a high recovery rate (e.g. 92%), it is necessary to subdivide the adsorbent column into a large number of beds (generally 24 beds) and limit the productivity of the unit. It has been demonstrated that for a charge containing approximately 20% p-xylene and 15% ethyl benzene, when wishing to obtain a p-xylene purity of 99.5% and a recovery rate of 92%, it is not possible to exceed a production of 0.04 m³ of p-xylene per cubic meter of adsorbent and per hour. The main disadvantage of these processes is the high investment due to the complexity of the unit. Another disadvantage is that a high solvent/charge ratio is necessary to obtain a high purity (min. 2.1 m³/m³), i.e. at least 10 m³ of solvent per m³ of p-xylene produced. This results in high energy costs for separating by distillation the solvent from the extract and the refined product.

Another process has been proposed (U.S. Pat. No. 3,939,221 of British Petroleum Chemical), which combines a first crystallization stage on a charge freed by distillation of a large part of the o-xylene and a second separation stage by simulated countercurrent liquid chromatography in order to p-xylene-deplete the mother liquor from the crystallization stage. This process is a simple juxtaposing of two existing processes, namely two-stage crystallization ($-65°$ C. and $-15°$ C.) and continuous liquid chromatography on a charge only containing 7 to 8% p-xylene. It does not lead to a simplification or to a fundamental modification of either of the two stages. It involves double the investment and its only advantage is to reduce the size of the isomerization loop, which is obtained equally well with the simulated countercurrent chromatography process alone.

The prior art is also illustrated by the following patents: EP-A-553622 describes a process for the preparation and separation of p-xylene with an adsorption stage on a silicate containing iron and optionally gallium and aluminium making it possible to obtain a first mixture containing p-xylene and ethyl benzene in a weight proportion of 1:1 and a second mixture containing o-xylene and m-xylene. The purification of this first mixture is performed at between $-15°$ C. and $-80°$ C. and more specifically at $-60°$ C. in the example.

British patent 1 420 796 describes a vapour phase $C_8$ aromatics separation process in at least two parallel zones. The adsorbate contains p-xylene and ethyl benzene in a substantially identical proportion and also contains 9% m-xylene. This adsorbate then undergoes crystallization.

U.S. Pat. No. 3,813,452 describes a process for the separation of a mixture containing $C_8$ and aromatics and $C_8$ non-aromatics supplying to a fractionation zone a non-aromatic head fraction containing 5% p-xylene. This head fraction undergoes a crystallization ($-40°$ to $-70°$ C.) and the p-xylene is recovered. Moreover, the $C_8$ aromatics-rich tail fraction is separated in an adsorption zone, optionally with simulated countercurrent and the p-xylene is recovered. In addition, the adsorption and crystallization are not linked.

JP-A-55-139 327 describes an adsorption of a $C_8$ aromatics mixture followed by a crystallization of the p-xylene obtained at between $+10°$ C. and $-20°$ C. However, the adsorption is carried out in a pseudo-moving bed having three zones, so that it is not possible to obtain a continuous circulation of the liquid. Moreover, the solvent rate on the charge reaches very high values (5:1 in the example). A suggestion is also made relative to a crystallization process with washing with high-purity p-xylene or water. This leads to a p-xylene content in the filtrate of at least 60% and therefore a lower extracted p-xylene yield. Under these conditions, the filtrate can only be reintroduced into the adsorption zone at a location different from that of the charge, the latter only containing 17 to 22% p-xylene.

SUMMARY OF THE INVENTION

The object of the invention is to obviate the above disadvantages. In general terms, the invention relates to a process for the separation and recovery of the p-xylene contained in a hydrocarbon charge essentially constituted by $C_8$ aromatic hydrocarbons, characterized in that is comprises the following stages:

a) continuous contacting takes place in at least one simulated moving bed adsorption zone of the charge containing m-xylene, p-xylene, ethyl benzene and optionally o-xylene with a zeolitic adsorbent bed in the presence of an appropriate desorption solvent, under adsorption conditions such that a first fraction is obtained, which contains solvent, m-xylene, ethyl benzene and optionally o-xylene and a second fraction containing solvent and essentially p-xylene with a purity between 75 and 98%;

b) the first fraction is distilled to separate the solvent on the one hand and the mixture of m-xylene, ethyl benzene and optionally o-xylene on the other;

c) said mixture is isomerized under appropriate conditions in the presence of hydrogen in an isomerization zone and an isomerate is recovered, which is recycled to stage a) after distilling it;

d) the second fraction is distilled and the solvent recovered on the one hand and the p-xylene with a purity of 75 to 98% on the other;

e) the p-xylene from stage d) is crystallized in a crystallization zone at a temperature between +10° C. and −25° C. and on the one hand a mother liquor is obtained, which is recycled to stage a) and on the other mother liquor-impregnated p-xylene crystals; and f) the p-xylene crystals are washed with an appropriate washing solvent in a washing zone and the p-xylene crystals with a very high degree of purity are recovered, namely generally at least 99.3% and preferably at least 99.7%.

Therefore the invention consists of combining in an original, simplified manner the two processes (liquid chromatography with continuous circulation of the liquid and crystallization in order to create more economic high-purity p-xylene production conditions). The simulated moving bed can be operated as a simulated countercurrent or a simulated cocurrent.

According to a characteristic of the process using the simulated moving bed, the operating conditions and choice of adsorbent are chosen in such a way that the first fraction corresponds to a refined product (the least selectively adsorbed compound) and the second fraction corresponds to an extract (the most selectively adsorbed compound).

According to another feature of the simulated moving bed process, the operating conditions and choice of the adsorbent are made in such a way that the first fraction is an extract and the second fraction is a raffinate.

In the process according to the invention, the charge is firstly treated by liquid chromatography, in accordance with a process described in U.S. Pat. No. 2,985,589, with simulated countercurrent, or according to a process described in U.S. Pat. No. 4,402,832, with a simulated concurrent, containing at least 4 zones. This patent states:

Another essential feature of the present invention is that inlets and outlets lying in the same zone are connected, as is also shown in FIG. 2, e.g., the outlet of the first separating unit is connected to the inlet of the second because that particular inlet and outlet both lie in zone IV. It should be noted with regard to the embodiment of the present invention shown in FIG. 2 that zones II and V lie in their entirety in the third and sixth separating units, respectively. The inlets and outlets of each of these two units are therefore connected to each other and the flow that occurs in both instances form these outlets to inlets is referred to as "pumparound." For reasons hereinafter discussed, those two embodiments of the invention having two separating units where pumparound occurs are the preferred embodiments. This procedure is used for inventively producing a low-purity p-xylene (75 to 98%, preferably 85 to 98%), which permits a considerably improved productivity (charge volume treated per adsorbent volume and per hour), a solvent to charge ratio lowered by at least one third, a p-xylene recovery rate of at least 98% and the use of a much smaller number of separate beds, e.g. the reduction can be from twenty four to eight. The increase in the p-xylene recovery rate means a reduction in the size of the isomerization loop both compared with the crystallization process and compared with the continuous liquid chromatography process. This avoids high recycling rates to the isomerization process and therefore avoids an overdimensioning of the isomerization separation loop.

According to the invention, in the second stage of the process, the second fraction of the first stage (already concentrated p-xylene) is purified. This stage corresponds to the final purification phase of the crystallization-based separation processes which are already commercially available (e.g. the ARCO process). For a second fraction containing 85 to 98% p-xylene, said crystallization is advantageously carried out at between +5° C. and −15° C. This avoids the prohibitive operating costs linked with the first crystallization stage, which makes it possible to continue to operate crystallization units which have become relatively uneconomic or technically superseded.

The mother liquor from the crystallization process can then be recycled to the first stage, i.e. to the supply system of the simulated moving bed chromatography system (countercurrent or cocurrent). In addition, the washing solvent for the p-xylene crystal cake can be redistilled. Among the crystal washing solvents use is e.g. possible of n-pentane, water, purified p-xylene or toluene.

According to a particularly advantageous performance procedure, it is also possible to create a synergism between the two stages (chromatography-crystallization), if the eluting solvent used in chromatography and the p-xylene crystal cake washing solvent used in crystallization is the same, when a single solvent distillation column is sufficient. This synergism clearly appears when using in preferred manner toluene as the common solvent to the two stages. This solvent has been described as an eluting solvent for the separation of xylenes with adsorbents mainly constituted by X or Y zeolites whose exchangeable sites are occupied by alkali metal or alkaline earth cations. Particularly good results are obtained with the Y zeolite exchanged both with barium (45 to 65% of the sites) and potassium (35 to 55%). Moreover, in the ARCO crystallization process, toluene can be used as the crystal cake washing solvent.

The juxtaposing of the two stages would involve a complete distillation of the first and second fractions of the simulated moving bed chromatography stage (with countercurrent or cocurrent) and a redistillation of the p-xylene washing toluene of the second crystallization stage. However, the integration of the two aforementioned stages of the process makes it possible to simplify the operations. Due to the fact that only reduced performance characteristics are required of the first stage with respect to the p-xylene purity, it is generally not disadvantageous to use an impure solvent as the desorption solvent. This impurity can be m-xylene contained in the washing toluene for the crystals of the second stage. The crystallization mother liquor can also contain a little toluene, which is not prejudicial when the latter is recycled to the first continuous chromatography stage. The distillation column of the second fraction containing the p-xylene of the first stage can be regulated with a reflux rate such that the toluene collected at the head contains up to 2% impure p-xylene and with a reboiling rate such that the impure p-xylene contains up to 3% toluene. The column for distilling the first fraction containing m-xylene and ethyl benzene of the first stage can also be regulated with a reflux rate such that the toluene contains up to 2% $C_8$ aromatics. It is preferable to leave toluene in the mixture of m-xylene, ethyl benzene and o-xylene supplied to the isomerization process, so as not to increase the size thereof. The reduction of the reflux rates of the columns makes it possible to minimize the size of the columns and therefore reduce the energy costs involved in separating the solvent. The solvent consumption for the complete process is also reduced. Generally, the charge is a hydrocarbon fraction with a boiling point between 136° and 145° C. When the charge contains o-xylene, the latter can be distilled in adequate conditions prior to stage a).

According to a feature of the process, the desorption solvent and the crystal washing solvent can be a solvent having a boiling point below that of the charge, such as toluene, or above that of the charge, such as cumene. As stated hereinbefore, preference is given to the use of toluene, because it is less expensive and is widely used in existing crystallization processes.

In this case, the solvent recovered in stage b) can be recycled to the adsorption zone and/or to the washing zone, the impure solvent resulting from the washing can be recycled to stage b) and/or stage d) (distillation) and the solvent resulting from the distillation stage d) can be recycled to the adsorption zone and/or to the washing zone.

According to another feature, the desorption solvent can be solvent having a boiling point higher than that of the charge, such as p-diethyl benzene and the washing solvent can be a solvent having a boiling point below that of the charge, such as toluene.

The solvent recovered in stages b) and d) can then be recycled to the adsorption zone and the impure solvent resulting from the washing undergoes a separate distillation suitable for supplying recycled pure solvent to the washing stage in the crystallization zone and a mixture of p-xylene, m-xylene, ethyl benzene and optionally recycled o-xylene to the adsorption stage.

The invention also relates to the apparatus and more particularly a unit for the separation and purification of the p-xylene contained in a hydrocarbon charge and essentially constituted by $C_8$ aromatic hydrocarbons. This unit comprises in combination:

a) a so-called simulated moving bed adsorption unit (8) (countercurrent or cocurrent) having a plurality of columns (6, 7) filled with a zeolitic adsorbent, a charge supply means (4), a recycled desorption solvent supply means (11), a means (10) for the discharge of the first fraction and a means (9) for the discharge of the second fraction, said adsorption unit being appropriate for the supply of the second fraction containing p-xylene with an appropriate purity and with improved productivity;

b) a first distillation unit (12) connected to the discharge means for the first fraction and having a head outlet (14) and a bottom outlet (15) and as a function of whether the solvent is lighter or heavier than the charge, the former will be drawn off at the head or bottom the unit and will at least partly be recycled by the means (11) to the adsorption unit, whereas the solvent-free first fraction will be discharged by said outlet (15);

c) an isomerization unit (21) having an inlet connected to the outlet (15) of the distillation unit (12) and an outlet supplying an isomerate connected to a third distillation unit (23) defined hereinafter;

d) a third distillation unit (23) able to supply by one outlet a distilled isomerate, which is recycled by appropriate means (2) to the adsorption unit and by another outlet light products produced during the isomerization stage; and e) a second distillation unit (16) connected to the p-xylene-containing second fraction discharge means (9) comprising, either at the top or at the bottom as a function of whether the solvent is lighter or heavier than the charge, an outlet (17) able to supply the desorption solvent, which is at least partly recycled by the recycling means (11) to the adsorption unit and a second outlet (19) able to supply p-xylene with a purity normally between 75 and 98%;

f) at least one unit (5) for the crystallization of the p-xylene from stage e) and which is connected to the outlet (19) able to operate at a temperature of $-25°$ C. to $+10°$ C., said crystallization unit also incorporating a unit for washing the crystals obtained having a supply (18) for an appropriate washing solvent, a first outlet supplying a mother solution recycled by the recycling means (3) to the adsorption unit and a second outlet (25) for the recovery of pure crystals.

According to a feature of the apparatus, the washing unit can comprise an impure solvent recovery line normally connected to a distillation member able to separate the pure solvent, which is generally recycled to the washing unit of the crystallization unit by a recycling line.

According to another feature of the apparatus, when the solvent recycled to the adsorption unit by the recycling means and the solvent recycled to the washing unit are one and the same solvent, the latter generally comes at least partly from the distillation unit for the second fraction and/or at least partly from the distillation unit of the first fraction, which can also distill the impure solvent as stated hereinbefore, which avoids extra costs and investment. Among the solvents which can be used, reference is made to mono-aromatic hydrocarbons described in U.S. Pat. No. 4,940,830, which give particularly good results.

According to another feature of the apparatus, the desorption solvent recycled to the adsorption unit can be p-diethyl benzene and the solvent recycled to the washing stage can be toluene. Under these conditions, the solution recovered at the bottom of the distillation means for the impure solvent is recycled to the adsorption unit by appropriate recycling means.

The operating conditions for the separating and recovery unit according to the invention are generally as follows:

In the case of a simulated countercurrent adsorption unit, the total useful length of the adsorption columns is normally between 10 and 30 meters and preferably between 15 and 25 m. This length is subdivided into a number of beds between 6 and 24 and preferably 8 and 12. The number of enclosures containing these beds is between 1 and the number of said beds and is preferably between 2 and 4. In addition, the number of zones (useful column length between an inlet and an outlet or vice versa) is at least 4. The temperature is generally between 140° and 185° C. and preferably between 150° and 175° C.

The average linear velocity related to the enclosure of the empty reactor is between 0.4 and 1.2 cm/s and in preferred manner between 0.8 and 1 cm/s. The solvent ratio (ratio of solvent flow to the charge flow) is between 1.20 and 2.5 and in preferred manner between 1.35 and 1.7. The recycling rate (ratio of the average recycling flow to the charge flow) is between 5 and 12 and preferably between 6 and 10.

To obtain p-xylene as an extract, when the desorption solvent is toluene, the preferred zeolite is a Y zeolite, such as is defined in U.S. Pat. No. 3,558,730 and in particular an exchange both with barium (45 to 65% of the sites) and potassium (35 to 55% of the sites) gives good results. However, when the desorption solvent is p diethyl benzene, the preferred zeolite is a X zeolite, as defined in U.S. Pat. No. 3,558,730. In particular, a quasi-total barium exchange with a residual sodium rate below 0.3% of the sites gives good results.

In both cases, the zeolite is advantageously used in the form of balls with a grain size between 0.25 and 1 mm diameter and preferably between 0.315 and 0.8 mm diameter. In both cases the water content of the zeolite is kept below 6% by weight and preferably below 3% by weight.

Among the X zeolites, that exchanged e.g. with Ba also permits a good separation as an extract of the p-xylene and the ethyl benzene as the major impurity. Among the Y zeolites selectively absorbing p-xylene, those exchanged with a single cation such as K. Rb, Cs, Ag (U.S. Pat. No. 4,044,062) or high pressure (HP) zeolites with lithium (U.S. Pat. No. 4,615,994) are the most widely used because of their good selectivity. Y and X zeolites exchanged with two cations K+Ba, K+Be, K+Mg, K+Rb, K+Cs, Rb+Ba, Cs+Ba, K+Cu give good results. It is also possible to use $\beta$, ZM11 or ZSM5 zeolites for selectively adsorbing p-xylene. In this case ethyl benzene will again be the major impurity. However, Y zeolites exchanged e.g. with Li,Na, Be, Mg, Ca, Sr, Mn, Cd, Cu, Ni or with a pair of ions such as Cu+Cd, Cu+Ag and Zn+Ag make it possible to selectively adsorb m-xylene and o-xylene and obtain a raffinate containing p-xylene in the majority (U.S. Pat. No. 4,044,062).

In the case of a simulated cocurrent adsorption unit, the operating conditions are essentially those used for simulated countercurrent, except that the column is subdivided into between 6 and 24 and preferably 6 and 12 beds and the recycling rate is between 0.8 and 7 and preferably between 4 and 5.5.

The choice of the adsorbent and the solvent is the same as described hereinbefore for obtaining p-xylene as the extract or as the raffinate. Simulated cocurrent operation makes it possible to obtain a low purity extract compatible with the process according to the invention.

In the case of a low-purity p-xylene crystallization unit, numerous processes are available and reference is e.g. made to the operating conditions of the ARCO process for a charge containing 85 to 90% p-xylene, a crystallizer temperature of +5° C. to −15° C., p-xylene purity of 99.75%, p-xylene yield of 88 to 94%, mother liquor p-xylene content 25 to 45%, washing rate 0.8 to 2 volumes of toluene per volume of p-xylene crystals and toluene content of the purified p-xylene prior to final distillation 80 to 98% by weight.

In the case of an isomerization unit for the first fraction constituted by a mixture of m-xylene, ethyl benzene and optionally o-xylene, numerous processes are available. Certain of these convert ethyl benzene into xylenes, such as the UOP and Engelhardt processes, which use a bifunctional catalyst based on platina on alumina and mordenite in H form, whilst another cracks ethyl benzene into benzene and ethylene and is in fact the Mobil process, which uses a catalyst based on a ZSM5 zeolite. For reference purposes, the operating conditions of the first class of processes are temperature 380° to 420° C., pressure 10 to 42 bar of hydrogen, space velocity 2 to 4 kg/kg/hour, $C_8$ aromatics conversion rate 92 to 98% and conversion rate of ethylene benzene into xylenes of 35 to 55%.

The invention will be better understood from the diagram illustrating in a non-limitative manner the process and apparatus.

The operating conditions and the adsorption are chosen in such a way that the first fraction containing the m-xylene and ethyl benzene is a raffinate and the second fraction essentially containing p-xylene is an extract. A line 1 is used for carrying a charge consisting of approximately 20% ethyl benzene, 18% p-xylene, 45% m-xylene and 17% o-xylene. With it is combined by a line 2 a recycled effluent, whose ethyl benzene content is significantly lower and typically 8 to 13% and which contains a non-aromatic impurities. By means of a line 3 introduction takes place of another recycled effluent, whose p-xylene content is higher, typically 25 to 45%. A line 4 recovers the charge and these two effluents and carries a mixture with the following approximate composition: 20 to 22.5% p-xylene, 9 to 14% ethyl benzene, 20 to 22.5% o-xylene and 45 to 50% m-xylene and which is introduced into a simulated countercurrent adsorption chromatography unit 8 having a limited number of columns 6 and 7 filled with a zeolitic adsorbent, each of the columns being subdivided into a limited number of sections (the total number of column sections being between 8 and 12), the productivity expressed relative to the p-xylene produced being approximately 0.08 m³/m³ of sieve and per hour under ambient conditions. Desorption takes place by toluene, at a rate of approximately 1.45 m³ of toluene per m³ of charge, the operating temperature being roughly 160° C. From this unit is drawn off a line 10 a p-xylene-depleted refined product essentially containing toluene, m-xylene, ethyl benzene and o-xylene and by a line 9 is drawn off an extract having a p-xylene enriched composition and which essentially contains toluene and p-xylene, the major impurity being ethyl benzene. The raffinate is introduced into a distillation column 12 (head temperature 125° C., bottom temperature 160° C., for example), in which is also recycled impure toluene by a line 13 coming from the washing unit of the crystallization unit referred to hereinafter. At the head and using a line 14, toluene is drawn off (approximately 37% of the introduced quantity), which e.g. contains less than 200 ppm of aromatic $C_8$ fraction and at the bottom of the column and using a line 14 is drawn off a liquid (solvent-free refined product), which is rich in ethyl benzene, m-xylene and o-xylene and depleted in p-xylene (e.g. less than 0.5%), which is fed into an isomerization unit 21. This refined product is contacted with hydrogen introduced by a line 20 and with a catalyst based on mordenite and platinium on alumina at approximately 380° C. A line 22 leads the isomerate from the reactor outlet to a distillation column 23 (top temperature 90° C., bottom temperature 160° C., for example). At the top are drawn off $C_1$ to $C_5$ hydrocarbons, hexane, cyclohexane, benzene and toluene and from the bottom of the column using a line 2, an effluent containing 8 to 13% ethyl benzene, 21 to 24% p-xylene, 21 to 24% o-xylene, 45 to 50% m-xylene and non-aromatic impurities, which is recycled to the adsorption liquid chromatography unit.

The line 9 introduces the extract into a distillation column 16, from which is drawn off at the top toluene with less than 0.2% aromatic $C_8$ fraction (approximately 63% of the quantity introduced, for example), which is recycled by the line 11 to the desorption solvent supply of the adsorption unit and to the crystallization unit. At the bottom of the column 16 and at approximately 160° C., low-purity p-xylene is drawn off (approximately 90% p-xylene) using a line 19, which passes it into a crystallization unit 5 operating at approximately −10° C. In said unit 5 production takes place on the one hand of a solution or a p-xylene-depleted mother liquor (approximately 38%), which is recycled by the line 3 to the intake of the liquid chromatography unit at the charge introduction point and on the other hand a mother liquor-impregnated p-xylene crystal cake. This cake is centrifuged and washed with toluene is a unit not shown in the drawing. The washing toluene is supplied by the line 18 and can come, as shown in the drawing, from the distillation unit for the raffinate 12 and/or the distillation unit for the extract 16. From the unit 5 is recovered melted p-xylene of purity 99.75% using a line 25 and impure toluene, which is fed by the line 13 to the distillation system 12.

Thus, a description has been given of an embodiment, where the desorption solvent of the adsorption unit and the washing solvent of the crystallization unit are one and the same, i.e. toluene.

In the case where p diethyl benzene is the desorption solvent and toluene the washing solvent, the distillation units 12 and 16 only supply solvent to the adsorption unit. A supplementary distillation member is then necessary for distillating the toluene used in the washing unit of the crystallization unit. This substantially pure toluene is then recycled to the washing unit, whilst the solution recovered at the bottom of the distillation column is combined with the mother liquor and recycled to the adsorption unit by the line 3.

EXAMPLE 1

This example illustrates a particular aspect of the invention, namely the simplification of the continuous liquid chromatography unit. A pilot continuous liquid chromatography unit was produced on the basis of 24 columns in a row with a length of 1 m and a diameter of 1 cm, the circulation between the 24th and the first column taking place by means of a recycling pump. At each intercolumn connection can be injected either a charge to be separated, or solvent. It is also possible to draw off either a raffinate, or an extract. This unit is described in an article entitled "Preparative and production scale chromatography processes with applications", published by G. Barker, G. Ganestos (Birmingham University, UK), chapter entitled "From batch elution to simulated countercurrent chromatography" by B. Balannec and G. Hotier (Publication of Marcel Dekker Inc., New York, 1992).

The absorbent is constituted by Y zeolite exchanged by potassium and barium, the exchange rate expressed in normality is approximately 50% for each of the two cations. The zeolite is used in the form of balls with a diameter of 0.315 to 0.5 mm. All the columns and distribution valves are placed in an oven at 150° C. Using the simulated countercurrent chromatography principle, there is an advance of three columns every six minutes in cocurrent with the circulation of liquid, the injection of solvent, the sampling of extract, the injection of the charge and the sampling the raffinate.

According to the invention, the number of beds to be considered is consequently eight. Six columns (i.e. two beds) are located between solvent injection and extract sampling, nine columns (three beds) between extract sampling and charge injection, three columns (one bed) between charge injection and raffinate sampling and the six final columns (two beds) are between raffinate sampling and solvent injection. Continuous injection (expressed at ambient conditions) takes place of 7.2 $cm^3$/min of toluene and 5 $cm^3$/min of charge incorporating 21% by weight p-xylene, 17% by weight ethyl benzene, 44% by weight m-xylene and 18% by weight o-xylene. There is also a continuous sampling of 5.40 $cm^3$/min of extract and 6.74 $cm^3$/min of raffinate and there are approximately 0.5% losses. During the first period of the cycle, of which there are eight, the solvent is injected in column 1, the extract is sampled at the outlet of column 6, the charge is injected in column 15 and the raffinate is sampled at the outlet from column 18. During the first two periods of the cycle, the recycling pump delivers, at ambient temperature, 38.7 $cm^3$/min, during the third period it delivers 45.5 $cm^3$/min and during the three following periods 40.5 $cm^3$/min and during the last two periods 45.9 $cm^3$/min. Thus, there is an average recycling flow rate of 42 $cm^3$/min., i.e. an average recycling rate of 8.4, based on the charge. The p-xylene, is obtained with a purity of 92.2% and a recovery rate of 98.1%. The temperature is 150° C. and the pressure decreases roughly linearly from 30 to 5 bar. The following table gives the steady state operation balance of the unit.

| Flow rate | Charge 5 $cm^3$/min | Solvent 7.2 $cm^3$/min | Extract 5.40 $cm^3$/min | Raffinate 6.74 $cm^3$/min |
|---|---|---|---|---|
| Toluene | — | 99.9% | 79.30% | 43.29% |
| Ethyl benzene | 17% | — | 1.07% | 11.72% |
| m-xylene | 44% | — | 0.40% | 32.30% |
| o-xylene | 18% | — | 0.15% | 12.40% |
| p-xylene | 21% | — | 19.08% | 0.29% |

The unit is limited to a total charge loss of 25 bar reached under these flow rate conditions. Under these conditions, the p-xylene productivity is 0.034 $m^3/m^3$ of sieve and per hour. In an industrial unit, the purity aimed at would only be 85% in an exemplified manner and the pressure drop resulting from the intercolumn links would be greatly reduced compared with the above pilot unit. It would thus be possible to increase the p-xylene productivity to 0.082 $m^3/m^3$/hour by multiplying all the rates by 1.5 and by reducing the switching period as a consequence (from 3.50 to 4 minutes approximately instead of 6 minutes) and finally by using a total useful length of 15 m instead of 24 m.

The simplified, simulated countercurrent adsorption liquid chromatography according to the invention is characterized by a high productivity compared with that industrially obtained according to the prior art (approximately 20% more in the pilot example shown and approximately 200% more in an industrial unit produced according to the invention). It is also covered by a higher p-xylene recovery rate and a significantly lower purity, these results being due to a solvent rate almost twice lower and a three times smaller number of injection and drawing off points, i.e. beds.

EXAMPLE 2

This example illustrates another special aspect of the invention, i.e. the p-xylene is produced in raffinate form. In the pilot unit of example 1 the adsorbent is constituted by a Y zeolite exchanged by strontium, the residual sodium rate expressed in normality is below 3.5%. As hereinbefore, the zeolite is used in the form of balls with a diameter of 0.315 to 0.5 mm. As in the case of example 1, there is an advance of three columns every six minutes cocurrent of the circulation of liquid, injection of the solvent, the sampling of extract, the injection of charge and the sampling of raffinate.

Thus, according to the invention the number of beds to be considered is eight. Six columns (i.e. two beds) are located between the solvent injection and the extract sampling, six columns between extract sampling and charge injection, six other columns between charge injection and raffinate sampling and the six final columns between raffinate sampling and solvent injection. Continuous injection takes place, under ambient conditions, of 6.8 cm³/min of toluene and 4 cm³/min of charge of example 1. Continuous sampling also takes place of 9.15 cm³/min of extract and 1.60 cm³/min of raffinate (i.e. approximately 0.5% losses). During the first period of the cycle, whereof there are eight, the solvent is injected in column 1, the extract sampled at the outlet from column 6, the charge injected in column 12 and the raffinate sampled at the outlet from column 18. During the first two periods of the cycle, the recycle pump, at ambient temperature, delivers 40.5 cm³/min, during the two following periods 42.4 cm³/min, during the fifth and sixth periods 38.4 cm³/min and finally during the two final periods of the cycle 47.3 cm³/min. Thus, there is an average recycling rate of 42.1 cm³/min, i.e. a recycling rate of 10.52, based on the charge. The p-xylene is obtained with a purity of 90.8% and a recovery rate of 96.85%, the temperature being 150° C. The following table gives the steady-state operation balance of the unit.

| Flow rate | Charge 4 cm³/min | Solvent 6.8 cm³/min | Extract 9.15 cm³/min | Raffinate 1.6 cm³/min | Losses 0.05 cm³/min |
|---|---|---|---|---|---|
| toluene | — | 99.9% | 66.27% | 44.00% | |
| ethyl benzene | 17% | — | 7.08% | 1.84% | |
| m-xylene | 44% | — | 18.86% | 1.71% | |
| o-xylene | 18% | — | 7.54% | 1.61% | |
| p-xylene | 21% | — | 0.25% | 50.84% | |

The delivery pressure of the recycling pump is 30 bar and is 5 bar on suction for the same pump.

EXAMPLE 3

This example illustrates a particular aspect of the invention, namely simulated cocurrent operation. The pilot unit and the adsorbent described in example 1 are again used. On the basis of the principle of simulated cocurrent chromatography, there is a moving back of four columns every eight minutes, i.e. countercurrent of the liquid circulation, the solvent injection, the extract sampling, the charge injection and the raffinate sampling.

According to the invention, the number of beds to be considered is no more than six. Eight columns (i.e. two beds) are located between solvent injection and extract sampling, four columns (i.e. one bed) between extract sampling and charge introduction, eight columns (i.e. two beds) between charge introduction and raffinate sampling and finally the four final columns (one bed) between raffinate sampling and solvent injection. Continuous injection takes place, under ambient conditions, of 10.35 cm³/min of toluene and 7.65 cm³/min of charge of example 1. Continuous sampling also takes place of 9.35 cm³/min of extract and 8.55 cm³/min of raffinate i.e. approximately 0.55% losses. During the first period of the cycle, whereof there are six, the recycling pump delivers, at ambient temperature, 35.5 cm³/min, during the two following periods the flow rate is 45.85 cm³min, during the four period the recycling rate is 36.5 cm³/min and during the final two periods of the cycle the pump delivers 44.15 cm³/min. Therefore there is an average recycling rate of 42 cm³/min, i.e., an average recycling level of 5.5, based on the charge. The p-xylene is obtained with a purity of 87.25% and a recovery rate of 99.10%. The temperature is 150° C. The following table gives the steady state operation balance of the unit.

| Flow rate | Charge 7.65 cm³/min | Solvent 10.35 cm³/min | Extract 9.35 cm³/min | Raffinate 8.55 cm³/min | Losses 0.1 cm³/min |
|---|---|---|---|---|---|
| toluene | — | 99.9% | 80.58% | 32.21% | |
| ethyl benzene | 17% | — | 1.23% | 13.79% | |
| m-xylene | 44% | — | 0.89% | 38.20% | |
| o-xylene | 18% | — | 0.36% | 15.63% | |
| p-xylene | 21% | — | 16.94% | 0.17% | |

EXAMPLE 4

The particular aspect of the invention illustrated in this example is the production of p-xylene as a refined product using simulated cocurrent operation. The pilot unit of example 1 is charged with a zeolite of example 2, whilst the distribution of the columns, beds and movements of the valves are identical to those of example 3.

Continuous injection takes place, expressed under ambient conditions, of 9.95 cm³/min of toluene and 5.85 cm³/min of charge of example 1. Continuous sampling takes place of 11.20 cm³/min of extract and 4.53 cm³/min of raffinate (i.e. approximately 0.5% losses). During the first period of the six cycles, the recycling pump delivers, at ambient temperature, 37.35 cm³min, during the two following periods 47.30 cm³/min, during the fourth period the recycling rate is 36.1 cm³/min and finally during the two last periods of the cycle the pump delivers 41.95 cm³/min. There is consequently an average flow rate of 42 cm³/min, i.e. an average recycling rate of 7.18, based on the charge. The p-xylene is obtained with a purity of 83.36% and a recovery rate of 97.44%, the temperature being 150° C. The following table gives the steady-state operation balance of the unit.

space velocity of 3.5 kg/kg/hour. This gives an effluent with the following composition by weight:

| light $C_1$ to benzene inclusive: | 2.35% |
| --- | --- |
| toluene: | 2.4% |
| naphthene: | 2.2% |
| ethyl benzene: | 10.95% |
| p-xylene: | 19.72% |
| m-xylene: | 42.65% |
| o-xylene: | 19.73% |

This corresponds to a $C_8$ aromatics conversion rate of 94.5% and an ethyl benzene conversion rate of 43%. It should be noted that it is not possible to remove the naphthene impurities from the isomerate. A stationary concentration of these species is established in the loop, said products being drawn off with the raffinate in the liquid chromatography unit.

The bottom of the extract column is fed into a crystal-

| Flow rate | Charge<br>5.85 cm³/min | Solvent<br>9.95 cm³/min | Extract<br>11.20 cm³/min | Raffinate<br>4.53 cm³/min | Losses<br>0.07 cm³/min |
| --- | --- | --- | --- | --- | --- |
| toluene | — | 99.9% | 60.76% | 68.44% | |
| ethyl benzene | 17% | — | 8.09% | 1.87% | |
| m-xylene | 44% | — | 22.18% | 1.74% | |
| o-xylene | 18% | — | 8.69% | 1.64% | |
| p-xylene | 21% | — | 0.28% | 26.31% | |

EXAMPLE 5

The extract and raffinate of example 1 are used and distilled continuously under the following conditions.

| | | EXTRACT | RAFFINATE |
| --- | --- | --- | --- |
| No. of real plates | | 40 | 32 |
| Top temperature | | 125° C. | 125° C. |
| Bottom temperature | | 161° C. | 161° C. |
| Reflux rate | | 1.14 | 1.06 |
| Composition by weight) | | | |
| Top | Toluene | 99.48 | Toluene 98.0 |
| | Ethyl benzene | 0.03 | Ethyl benzene 0.41 |
| | p-xylene | 0.48 | p-xylene 0.01 |
| | m-xylene | 0.01 | m-xylene 1.14 |
| | o-xylene | 0.004 | o-xylene 0.44 |
| Botton | Toluene | 2.00 | Toluene 1.53 |
| | Ethyl benzene | 5.07 | Ethyl benzene 20.35 |
| | p-xylene | 90.33 | p-xylene 0.50 |
| | m-xylene | 1.89 | m-xylene 56.09 |
| | o-xylene | 0.71 | o-xylene 21.53 |

The solvent reinjected into the liquid chromatography unit (constituted by effluents passing out at the column head) have the following operation: 98.95% toluene, 0.21% ethyl benzene, 0.40% m-xylene, 0.15% o-xylene and 0.29% p-xylene, which will only affect very slightly the extract and raffinate compositions obtained in example 1 with 99.9% pure toluene. However, this makes is possible to very significantly reduce the number of plates and the reflux and reboiling rates required by said two columns compared with the case where they would have to produce 99.9% toluene. The bottom of the raffinate column is isomerized on a bifunctional platinum on alumina and mordenite catalyst at 390° C., under a hydrogen pressure of 20 bar and a lization unit operation at −8° C. Collection takes place on the one hand of a mother liquor containing approximately 38.5% p-xylene, which is recycled to the intake of the liquid chromatography unit and on the other hand a mother liquor-impregnated crystal cake, which is rewashed with toluene from the extract distillation column (1.15 toluene volume per cake volume). After said washing, a p-xylene cake is collected, which has a toluene content of approximately 3.1% by weight and 1.13 liquid volume containing approximately 30% mother liquor, which is fed to the raffinate distillation column.

The p-xylene obtained has a purity of 99.8%. The final purification by crystallization using toluene produced by one of the distillation columns of the chromatography unit, so that the crystallization stages only requires one distillation column for the final separation of the p-xylene and the toluene. Therefore the combination of the stages of the process according to the invention makes it possible to minimize the size of the distillation columns and therefore their energy consumption. It also makes it possible to reduce the solvent consumption.

In a similar way, the raffinate and extract produced in examples 2, 3 and 4 are continuously distilled. The substantially solvent-free raffinate is isomerized under the conditions defined hereinbefore, whilst the substantially solvent-free extract is fed into the aforementioned crystallization unit, with which production takes places of 99.8% p-xylene and a mother liquor, which is fed to the simulated moving bed chromatography stage.

We claim:

1. An apparatus for the separation and recovery of p-xylene contained in a $C_8$-aromatic hydrocarbon charge comprising in combination:
   a) a simulated moving bed adsorption unit (8) having a plurality of columns (6,7) filled with a zeolitic adsorbent, a means (4) for supplying a charge, a means (11) for supplying a desorption solvent, a means (10) for the discharge of a first fraction and a means (9) for the discharge of a second fraction containing p-xylene, said adsorption unit being able to supply said second fraction with a purity and with an improved productivity relative to said $C_8$-aromatic hydrocarbon charge;

b) a first distillation unit (12) connected to said means for the discharge of the first fraction and having a first outlet (14) able to supply the desorption solvent which is recycled at least partly by said desorption solvent supply means (11) to the adsorption unit and a second outlet (15) able to supply a solvent-free raffinate;

c) an isomerization unit (21) having an inlet connected to the outlet (15) of the distillation unit (12) and an outlet supplying an isomerate;

d) a second distillation unit (16) connected to said means (9) for discharging the second fraction containing the p-xylene, and having an outlet (17) connected to said desorption solvent supply means (11) able to supply the desorption solvent, which desorption solvent is at least partly recycled to the adsorption unit and a second outlet (19) able to supply p-xylene with a purity normally between 75 and 98%;

e) a third distillation unit (23) connected to said outlet supplying an isomerizate, said second distillation unit being able to supply a distilled isomerate, which is recycled by recycle means (2) to the adsorption unit, and by another outlet (24) light products produced during the isomerization;

f) at least one unit for the crystallization of the p-xylene of stage d) connected to said second outlet (19) and being able to operate at a temperature of −25° C. to +10° C., said crystallization unit also comprising a unit for washing p-xylene crystals obtained and which has a supply means (18) for an appropriate washing solvent, a first outlet for supplying a mother solution recycled by a recycling means (3) to the adsorption unit and a second pure crystal recovery outlet (25); the p-xylene separation and recovery unit having a washing solvent line (18) which connects the outlet (17) of the first distillation unit and/or the first outlet (14) of the second distillation unit (12) to the crystal washing unit, the washing unit being connected by an impure solvent recovery time (13) to the first distillation unit able to separate substantially pure solvent from impure solvent.

2. Unit according to claim 1, wherein the recycling means (3) are connected to the means for supplying charge to the columns (6).

3. Unit according to claim 1, wherein the simulated moving bed adsorption unit is a simulated countercurrent bed.

4. Unit according to claim 1, wherein the simulated moving bed adsorption unit is a simulated cocurrent bed.

5. A unit according to claim 4, wherein the columns of the simulated moving bed adsorption unit are connected so as to form two separate closed loops.

6. A unit according to claim 4, wherein the columns of the simulated moving bed adsorption unit are connected so as to form a single closed loop.

* * * * *

UNITED STATES PATENT AND TRADEMARK OFFICE
CERTIFICATE OF CORRECTION

PATENT NO. : 5,401,476
DATED : March 28, 1995
INVENTOR(S) : Gerard HOTIER et al.

It is certified that error appears in the above-indentified patent and that said Letters Patent is hereby corrected as shown below:

Claim 1; Column 16, line 14: After recovery change "time" to -- line --.

Signed and Sealed this

Eighteenth Day of July, 1995

Attest:

BRUCE LEHMAN

*Attesting Officer*  *Commissioner of Patents and Trademarks*